(12) United States Patent
Schatz

(10) Patent No.: US 9,662,458 B2
(45) Date of Patent: May 30, 2017

(54) INJECTION NEEDLE INSERTION BARRIER

(71) Applicant: Richard A. Schatz, San Diego, CA (US)

(72) Inventor: Richard A. Schatz, San Diego, CA (US)

(*) Notice: Subject to any disclaimer, the term of this patent is extended or adjusted under 35 U.S.C. 154(b) by 0 days.

(21) Appl. No.: 14/644,808

(22) Filed: Mar. 11, 2015

(65) Prior Publication Data

US 2015/0202381 A1 Jul. 23, 2015

Related U.S. Application Data

(60) Continuation-in-part of application No. 14/079,841, filed on Nov. 14, 2013, now abandoned, which is a division of application No. 12/977,737, filed on Dec. 23, 2010, now abandoned.

(51) Int. Cl.

| | |
|---|---|
| *A61M 5/46* | (2006.01) |
| *A61M 25/00* | (2006.01) |
| *A61B 17/34* | (2006.01) |
| *A61M 25/01* | (2006.01) |
| *A61B 90/00* | (2016.01) |

(52) U.S. Cl.
CPC ........... *A61M 5/46* (2013.01); *A61B 17/3478* (2013.01); *A61M 25/0074* (2013.01); *A61M 25/0084* (2013.01); *A61M 25/0108* (2013.01); *A61B 2090/036* (2016.02); *A61M 2025/0089* (2013.01); *A61M 2025/0096* (2013.01)

(58) Field of Classification Search
CPC ................ A61M 5/46; A61M 25/0074; A61M 25/0084; A61M 25/0108; A61M 2025/0089; A61M 2025/0096; A61B 17/3478; A61B 17/3494; A61B 2018/00279

See application file for complete search history.

(56) References Cited

U.S. PATENT DOCUMENTS

| | | |
|---|---|---|
| 5,951,568 A | 9/1999 | Schatz |
| 5,964,778 A | 10/1999 | Fugoso et al. |
| 6,039,727 A * | 3/2000 | Javier, Jr. ............... A61B 18/22 606/10 |
| 7,285,108 B2 | 10/2007 | Koerner et al. |

(Continued)

FOREIGN PATENT DOCUMENTS

WO 2012087507 A1 6/2012

OTHER PUBLICATIONS

European Search Report, EU Application No. 15172328.5, Jun. 16, 2015.

*Primary Examiner* — Kami A Bosworth
(74) *Attorney, Agent, or Firm* — Nydegger & Associates

(57) ABSTRACT

A catheter system includes a positioning catheter for receiving an injection needle into its lumen. Structurally, the injection needle incorporates a plurality of loops that are mounted directly onto its shaft. As the injection needle is moved in a distal direction to exit from the lumen of the catheter, the loops are individually biased to transition from a folded configuration, and into a deployed configuration. In their deployed configurations, the loops create a barrier that is oriented perpendicular to the needle. Thus, the barrier acts to limit the depth of insertion of the needle into target tissue of a patient, to a predetermined depth, and to prevent perforation of the target tissue by the catheter tip.

12 Claims, 3 Drawing Sheets

(56) References Cited

U.S. PATENT DOCUMENTS

| | | |
|---|---|---|
| 7,803,136 B2 | 9/2010 | Schatz |
| 2002/0120250 A1 | 8/2002 | Altman |
| 2003/0028172 A1 | 2/2003 | Epstein et al. |
| 2006/0142697 A1 | 6/2006 | Hawk et al. |
| 2007/0055180 A1 | 3/2007 | Deem et al. |
| 2009/0227892 A1 | 9/2009 | Krombach et al. |
| 2010/0145306 A1 | 6/2010 | Mickley et al. |
| 2010/0179567 A1 | 7/2010 | Voss et al. |
| 2010/0191222 A1 | 7/2010 | Schatz |
| 2012/0165785 A1 | 6/2012 | Schatz |
| 2014/0081207 A1 | 3/2014 | Schatz |

\* cited by examiner

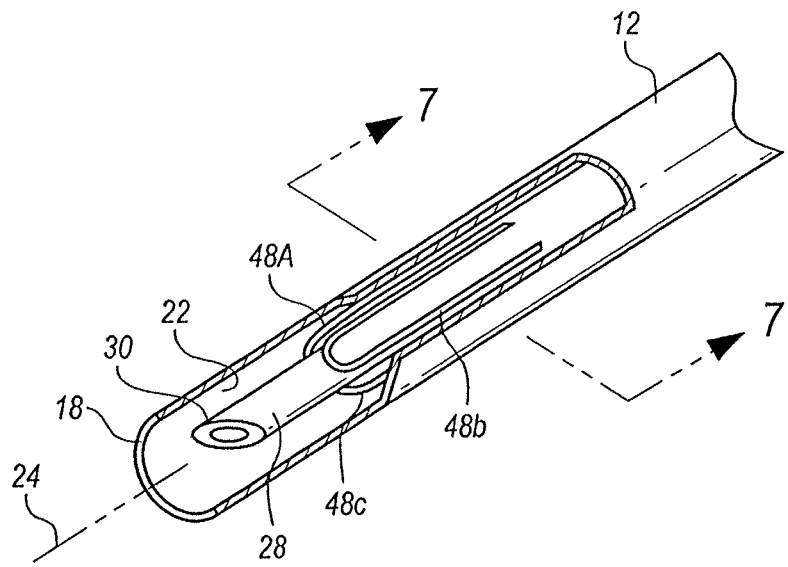
FIG. 6A
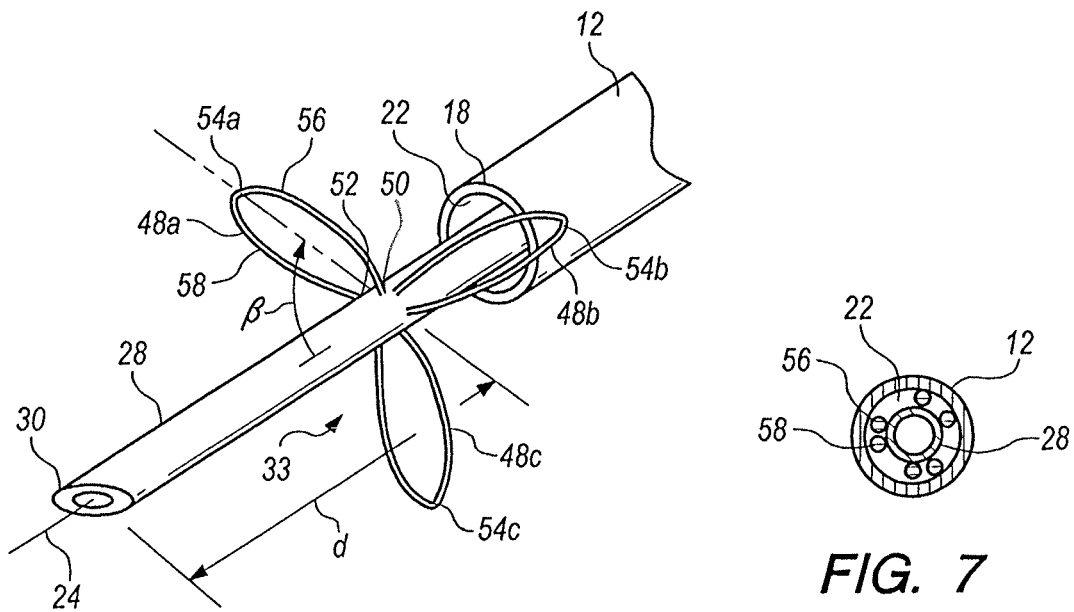
FIG. 6B
FIG. 7

INJECTION NEEDLE INSERTION BARRIER

This application is a continuation-in-part of application Ser. No. 14/079,841, filed Nov. 14, 2013, which is now abandoned, and which is a divisional of application Ser. No. 12/977,737, filed Dec. 23, 2010, which is now abandoned. The contents of application Ser. Nos. 14/079,841 and 12/977,737 are incorporated herein by reference.

FIELD OF THE INVENTION

The present invention pertains generally to injection catheters. More particularly, the present invention pertains to systems and methods for injecting fluid medicaments into myocardial tissue, and other internal tissue of a patient. The present invention is particularly, but not exclusively, useful as a system and method having a catheter-based injection needle that incorporates mechanical means to limit needle insertion into tissue to within a predetermined depth and to prevent perforation of the catheter tip through the wall of the tissue.

BACKGROUND OF THE INVENTION

Injecting fluid medicaments into internal tissues of the body (e.g. the myocardium) can be problematic. This is particularly so due to the fact there is no way for the surgeon to have a direct visualization of the injection site. Although indirect visualization techniques, such as fluoroscopy, can significantly aid in advancing an injection needle to the intended injection site, additional control at the site may be required in order to properly insert a needle into tissue for a precise injection. For instance, control over the depth to which an injection needle is inserted into the tissue may be a crucial consideration. Further, and specific to the heart, perforation of the catheter tip through the heart wall causes blood to leak into the pericardial sack, which can be fatal.

As a practical matter, a reliance on extracorporeal control over an injection needle, for the specific purpose of precisely attaining a desired depth of needle insertion into tissue, is complicated by several factors. Not the least of these involves the proper positioning of the injection needle at the target tissue site, before needle insertion. Typically, such a pre-positioning of an injection needle can be successfully accomplished using a positioning catheter that incorporates radiopaque markers (e.g. fluoroscopy). Nevertheless, this pre-positioning relies on only indirect visual indicators that may fail to provide sufficient control for inserting the needle into target tissue.

In light of the above, it is an object of the present invention to provide a system and method for performing an injection of fluid medicament into a target tissue of a patient that provides for tactile indications of a proper needle insertion. Another object of the present invention is to ensure that such a needle insertion is performed to within a precise depth into the target tissue and to prevent perforation of the tissue by the catheter tip. Still another object of the present invention is to provide a system and method for performing an injection of fluid medicament into a target tissue that is relatively simple to manufacture, is easy to use, and is comparatively cost effective.

SUMMARY OF THE INVENTION

In accordance with the present invention, a catheter-based injection needle is provided that controls the depth to which the needle can be inserted in an internal target tissue of a patient (e.g. the myocardium). For the purpose of controlling the insertion depth of the needle, a web member (barrier) is mounted onto the shaft of the needle at a distance "d", proximal to the distal end of the needle. During a procedure (i.e. an injection of a fluid medicament), this web member is caused (biased) to flare outwardly from the needle. With the web member in this flared configuration, an advancement (insertion) of the needle into the target tissue is limited. Specifically, insertion of the needle is limited to the distance "d". More specifically, this happens when the barrier makes contact with a surface of the target tissue. As envisioned for the present invention, the distance "d" can be varied according to the particular procedure being employed and the desires of the user.

Structurally, a system in accordance with the present invention includes a hollow positioning catheter having a lumen that extends between a proximal end and a distal end of the catheter. Also included in the system is the injection needle mentioned above. For purposes of the present invention, the injection needle is dimensioned to be received into the lumen of the positioning catheter for back-and-forth (proximal-and-distal) movements in the lumen. Further, the web member is dimensioned to pass through the lumen of the catheter along with the injection needle. To do this, the web member is confined by the positioning catheter to assume a folded configuration inside the lumen of the positioning catheter. While the web member is held by the positioning catheter in its folded configuration, the web member is substantially cylindrical shaped and is oriented parallel to the co-axis of the needle and the catheter. With the web member in this folded configuration, and with the positioning catheter pre-positioned in the vasculature of a patient, the injection needle can be advanced through the positioning catheter to the site of the target tissue. Alternatively, if the positioning catheter is not pre-positioned in the vasculature of the patient, the injection catheter can be advanced into the vasculature together with the positioning catheter. In either case, once the system is adjacent the target tissue site, the injection needle and web member are deployed from the distal end of the positioning catheter.

When the injection needle is deployed from the distal end of the positioning catheter, the web member is no longer constrained by the catheter, and it is biased into its flared configuration. As envisioned for the present invention, a deployment of the injection needle (web member) can be accomplished either by withdrawing the catheter in a proximal direction relative to the injection needle, or by advancing the injection needle in a distal direction relative to the catheter. Regardless how it is deployed, when it is in its flared configuration, the web member establishes a disk-shaped barrier that is oriented substantially perpendicular to the co-axis of the catheter and the needle. As indicated above, this barrier is located at the selected distance "d" from the distal end of the injection needle. As also indicated above, the purpose here is to limit the insertion depth of the injection needle to the distance "d". Also, when deployed, the barrier acts to prevent any distal movement of the catheter beyond the barrier, to thereby prevent the catheter tip from perforating the target tissue. Once an injection has been completed, the injection needle can be withdrawn into the lumen of the catheter. Inside the lumen, the web member will again assume its folded configuration. The system can then be removed from the patient.

Several different structural arrangements for the barrier that is established by the web member in its flared configuration are envisioned for the present invention. These include an arrangement wherein the web member comprises a plurality of elongated extensions, with each extension having a first end mounted on the injection needle. For this arrangement, each extension is biased to move the opposite (second) end radially outward from the axis with a deflection of the extension. Another possible arrangement for the web member includes a plurality of interconnected straight wires. In this arrangement, a first plurality of base wires will each have an end attached to the needle. A second plurality of wires will then have each of their ends attached to a respective base wire to thereby interconnect the base wires. Also, in another arrangement, the web member may comprise a plurality of elongated wire loops. Further, for each of the web member arrangements, the barrier will have a diameter "D" in its flared configuration and, typically, "D"/2 will be less than "d". As mentioned above, however, for some procedures it may be desirable for "d" to be less than "D"/2. In other aspects of the invention, the barrier can be radiopaque and made of a material such as cobalt chromium, platinum, nitinol or stainless steel. Also, the injection needle will preferably be less than or equal to 18 gauge, and the variously selected distance "d" will generally be less than 15 mm.

In another embodiment of the present invention a catheter system for performing an injection of fluid medicament into a tissue of a patient is provided which creates a web member with a penetration depth barrier for an injection needle. Specifically, for this embodiment, the web member comprises a plurality of loops. Like other embodiments of the present invention, this embodiment includes a positioning catheter having a proximal end and a distal end which has a lumen extending between the ends. Also included is an injection needle that is positioned in the lumen of the catheter for reciprocating movement through the lumen. Structurally, the injection needle has a proximal end and a distal end, and it defines a longitudinal axis.

For this embodiment of the present invention, each loop in the barrier of the web member is essentially an elongated wire having a first end and a second end which are bent around a midpoint of the wire to define a loop plane. In combination with the injection needle, the two ends of each loop are affixed to the needle at respective points in a plane that is perpendicular to the axis of the needle. Further, each loop is affixed to the needle to avoid any overlap or interference with another loop during an operation of the catheter system.

An important function for this embodiment of the present invention is that each loop of the web member is biased to transition in the loop plane between a folded configuration and a deployed configuration. In detail, for its folded configuration each loop has a first portion that extends between the first end of the loop and the midpoint. It also has a second portion that extends between the second end of the loop and the midpoint. In the folded configuration, the first portion is aligned substantially parallel to the second portion. For the deployed configuration of the web member, however, the first portion and the second portion of each loop are bowed away from each other to form an oval-shaped loop. To perform a transition between these configurations, the injection needle is moved axially relative to the catheter.

In its folded configuration each loop of the web member is constrained inside the lumen of the catheter. When the web member has been advanced in a distal direction beyond the distal end of the catheter, however, the web member is no longer constrained by the catheter and each loop transitions into its deployed configuration. It is also to be noted that during the configuration transition of a loop, its loop plane is rotated through a deployment angle β about an axis perpendicular to the axis of the needle. The consequence here is that during their configuration transition the loops (i.e. web member) are deployed to create a barrier which is established with the midpoints of each loop located at a distance "d" proximal the distal end of the injection needle. With this deployment, the system of the present invention prevents an insertion of the needle any deeper than the distance "d" into the tissue of the patient.

As envisioned for the present invention, when the injection needle is withdrawn inside the lumen of the catheter, and each loop in the web member is constrained by the catheter into its folded configuration, β will equal 0°. On the other hand, when the web member has been advanced beyond the distal end of the catheter, each loop is biased through the configuration transition from its folded configuration and into its deployed configuration to create the barrier. In this deployed configuration, the deployment angle β will typically be in a range between 60° and 90°.

In addition to the above disclosure for a web member that is created by a plurality of loops, it is also envisioned that in a preferred embodiment, the loops of the web member will be radiopaque and made of a material such as cobalt chromium, platinum, nitinol or stainless steel. Further, the injection needle will preferably be less than or equal to 27 gauge, and the distance "d" established for the barrier of the web member will be less than about 15 mm.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6A is a perspective view of a preferred embodiment of the present invention, with a plurality of loops constrained inside a catheter in a respective folded configuration, with portions of the catheter broken away for clarity;

FIG. 6B is a view of the present invention as shown in FIG. 6A with the plurality of loops advanced distally beyond the distal end of the catheter with the loops biased into their respective deployed configuration; and FIG. 7 is a cross-section view of the catheter system as seen along the line 7-7 in FIG. 6A.

DESCRIPTION OF THE PREFERRED EMBODIMENTS

Figure 1:
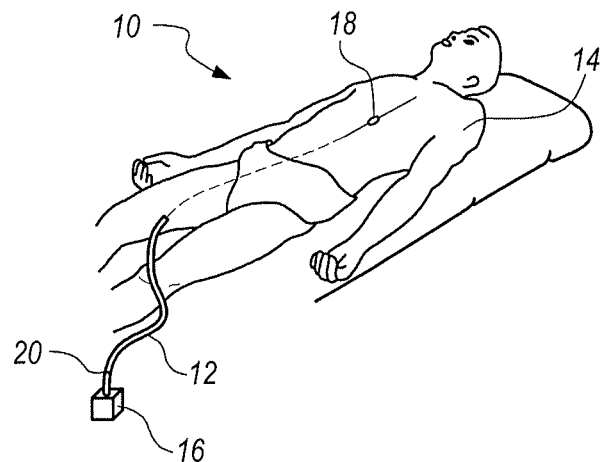
FIG. 1 is a perspective view of a system of the present invention shown in an intended operational environment.

Referring initially to FIG. 1, a system in accordance with the present invention is shown in its intended operational environment and is generally designated 10. As shown, the system 10 includes a catheter 12 that can be advanced into the vasculature of a patient 14. Also, the system 10 includes a source 16 of a fluid medicament that is to be injected into an internal tissue of the patient 14 (e.g. the myocardium). For the system 10, the catheter 12 is preferably a positioning type catheter 12 having a distal end 18 and a proximal end 20, with a lumen 22 that extends along the length of the catheter 12 between the ends 18/20. As indicated in FIG. 2, the catheter 12 defines a longitudinal axis 24.

Figure 2:
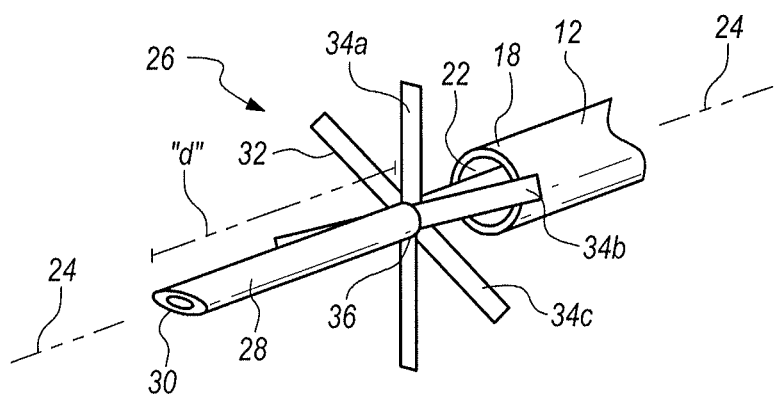
FIG. 2 is a perspective view of the system with the injection needle deployed from the distal end of a positioning catheter, and with the web member biased into its flared configuration.

FIG. 2 shows an injection assembly for the present invention that is generally designated 26. More specifically, the injection assembly 26 includes an injection needle 28 that has a distal end 30. Preferably, the injection needle 28 is less than or equal to 27 gauge. Additionally, the injection assembly 26 includes a web member 32 that is fixedly mounted on the injection needle 28 at a distance "d" proximal to the distal end 30 of the injection needle 28. Typically, the distance "d" will be less than ten millimeters. In other embodiments, however, the distance "d" can be adjustable. Stated differently, the exact length for distance "d" can be varied as required for the particular procedure (e.g. 3-7 mm).

For the preferred embodiment of the web member 32 shown in FIG. 2, the web member 32 includes a plurality of elongated extensions 34, of which the extension 34a, 34b and 34c are exemplary. In detail, an end of each extension 34 is affixed to the injection needle 28 at a location 36 (i.e. at the distance "d" from distal end 30). As intended for the system 10, all of the extensions 34 of web member 32 are biased to assume the position shown in FIG. 2. Specifically, each of the extensions 34 is biased to become oriented substantially perpendicular to the axis 24 when it is unrestrained. Consequently, under these unrestrained conditions, the web member 32 assumes a flared configuration that is generally disk-shaped, as shown in FIG. 2. In addition to its flared configuration, however, the web member 32 can be mechanically restrained to assume a folded configuration (see FIG. 3).

Figure 3:
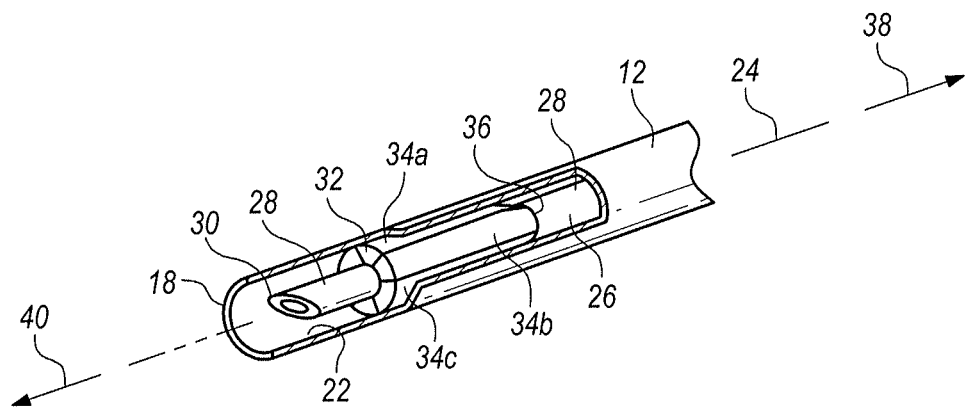
FIG. 3 is a perspective view of the system with the injection needle withdrawn into the lumen of the positioning catheter, and with the web member constrained by the positioning catheter into its folded configuration.

As shown in FIG. 3, when the injection assembly 26 is positioned inside the lumen 22 of catheter 12, all of the extensions 34 are forced to become individually aligned, and oriented substantially parallel to the axis 24. Under these conditions, the web member 32 becomes cylindrical shaped, to assume a folded configuration. For purposes of the present invention, it is important that the injection assembly 26 be moveable back-and-forth (i.e. proximal-and-distal) through the lumen 22 of the catheter 12, when the web member 32 is in its folded configuration.

As envisioned for the present invention, the web member 32 can be selectively transitioned between its flared configuration (FIG. 2) and its folded configuration (FIG. 3). For the system 10, this transition can be accomplished in either of two ways. For one, starting with the web member 32 in the folded configuration (FIG. 3), the catheter 12 can be withdrawn in a proximal direction (arrow 38) relative to the injection assembly 26. The consequence here is that when the distal end 30 of the injection needle 28 is more than the distance "d" from the distal end 18 of the catheter 12, the web member 32 is biased into its flared configuration (FIG. 2). For another, again starting with the web member 32 in its folded configuration, the injection assembly 26 can be advanced in a distal direction (arrow 40) relative to the catheter 12. Likewise, when the distal end 30 of the injection needle 28 is more than the distance "d" from the distal end 18 of the catheter 12, the consequence is that the web member 32 will assume its flared configuration. To return the web member 32 from its flared configuration to its folded configuration, these operations simply need to be reversed in order to retract the injection assembly 26 into the lumen 22 of the catheter 12.

Figure 4:
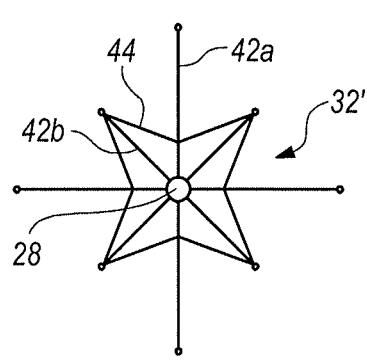
FIG. 4 is a front elevation view of an alternate embodiment of the web member.
Figure 5:
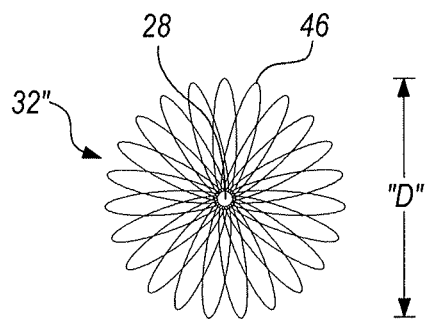
FIG. 5 is a front elevation view of another alternate embodiment of the web member.

Two different alternate embodiments of the web member 32, each of which is envisioned for use with the system 10, are respectively shown in FIG. 4 and FIG. 5. In FIG. 4 an alternate embodiment of a web member 32' is shown to include a plurality of base wires 42, and a plurality of interconnect wires 44. More specifically, for the web member 32', each base wire 42 will have an end that is connected directly onto the injection needle 28. The interconnect wire 44, on the other hand, will have its opposite ends connected to adjacent base wires 42 (e.g. base wires 42a and 42b). In FIG. 5, the web member 32" is shown to include a plurality of loops 46. For this embodiment, each loop 46 is connected to the injection needle 28. As shown in FIG. 4 and FIG. 5, the respective web members 32' and 32" are shown in their respective flared configurations. In this configuration, all embodiments (i.e. web member 32, web member 32' and web member 32") will establish a diameter "D" for its disk-shape. In most instances, "D"/2 will be less than "d", but it may happen that it is desirable for "d" to be less than "D"/2. Preferably, the barrier that is created by the web member 32, 32' or 32" is radiopaque and is made of cobalt chromium, platinum, nitinol or stainless steel.

In an operation of the system 10, the positioning catheter 12 can be pre-positioned in the vasculature of patient 14, or the injection assembly 26 can be inserted into the lumen 22 of the catheter 12 and this combination can be advanced into the vasculature. In either case, once the distal end 18 of the positioning catheter 12 is positioned at an injection site, adjacent to the target tissue (not shown), the injection assembly 26 is deployed from the catheter 12 (i.e. there is a transition of the injection assembly 26 as shown in FIG. 3 to how it is shown in FIG. 2). With this deployment, the web member 32 becomes unrestrained and is biased into its flared configuration (see FIG. 2). Thus, this flared configuration effectively establishes a barrier at the distance "d" from the distal end 30 of the injection needle 28.

With the injection assembly 26 configured as shown in FIG. 2, the injection needle 28 is inserted into the target tissue. As indicated above, the target tissue is envisioned as being either internal tissue, such as the myocardium, or external tissue like skin. Importantly, however, in each instance, the depth of this insertion into the target tissue is limited to the distance "d" by the barrier that is created when the web member 32 is biased into its flared configuration. Fluid medicament from the source 16 can then be injected into the patient 14.

Once the injection of fluid medicament has been completed, the injection needle 28 is withdrawn from the target tissue. The injection assembly 26 can then be retracted into the lumen 22 of catheter 12 until the barrier is collapsed when the web member 32 is returned to its folded configuration. The system 10 can then be removed from the patient 14.

In FIGS. 6A, 6B and 7, another embodiment of the present invention is shown. As clearly shown in FIGS. 6A and 6B, this embodiment includes a web member 33 (see FIG. 6B) which comprises a plurality of independent loops 48. In FIGS. 6A and 6B, the independent loops 48a, 48b and 48c are shown as examples of the plurality of such loops 48 that may be used.

A comparison of FIG. 6A with 6B shows that the web member 33 can have two different configurations. For its folded configuration, as shown in FIG. 6A, the independent loops 48a, 48b and 48c of the web member 33 are constrained by the guiding (positioning) catheter 12 inside the lumen 22 of the catheter 12. On the other hand, for its deployed configuration, as shown in FIG. 6B, the independent loops 48a, 48b and 48c of the web member 33 are not constrained by the guiding (positioning) catheter 12 inside the lumen 22 of the catheter 12. Instead, for the deployed configuration, the web member 33 that is affixed to the injection needle 28 has been advanced beyond the distal end 18 of the catheter 12 to a point where the independent loops 48a, 48b and 48c are biased into the deployed configuration.

The structural details of each independent loop 48 will, perhaps, be best appreciated with specific reference to the independent loop 48a in FIG. 6B. There it will be seen that the independent loop 48a is essentially an elongated wire having a first end 50 and a second end 52. As shown, this wire is bent around a midpoint 54 and the ends 50 and 52 of the wire are affixed to the injection needle 28 by any suitable means well known in the art, such as by welding. The consequence of this combination of structure is that the ends 50 and 52, together with the midpoint 54 of the independent loop 48 define a loop plane. Further, as indicated in FIG. 6B, during a configuration transition between a folded configuration of the web member 33 (FIG. 6A) and a deployed configuration (FIG. 6B), the loop plane defined by each respective independent loop 48 will rotate through a deployment angle β. As also shown in FIG. 6B, the independent loop 48a, which is exemplary of all such loops 48, defines a first portion 56 that extends between the first end 50 and the midpoint 54a of the loop 48a. Likewise, a second portion 58 extends between the second end 52 and the midpoint 54a of the loop 48a.

For a detailed disclosure of a configuration transition of the web member 33 between its folded and deployed configurations, reference is variously made to FIG. 6A, 6B or 7. In this cross reference it is to be appreciated that, although the disclosure here is primarily directed to a transition from the folded configuration (FIG. 6A) to the deployed configuration (FIG. 6B), the present invention also envisions transitions from the deployed configuration (FIG. 6B) to the folded configuration (FIG. 6A).

With the above in mind, FIG. 6A shows each of the independent loops 48a, b and c individually constrained within the lumen 22 of the guiding catheter 12. In this configuration, each loop 48 is stressed with their respective first portion 56 substantially parallel with the second portion 58 (cross reference FIG. 6A with FIG. 7). It should also be noted that when a loop 48 is constrained into its folded configuration, the deployment angle of its loop plane will be essentially zero (i.e. β=0°). On the other hand, when the web member 33 is deployed, its independent loops 48a, b and c are biased into an unstressed state (i.e. they are unconstrained by the catheter 12) and each loop 48 will assume an elliptically shaped configuration. Stated differently, in a deployed configuration (i.e. unconstrained) the first portion 56 and the second portion 58 are bowed away from each other. Furthermore, as indicated in FIG. 6B, the respective loop plane of each independent loop 48 is rotated with respect to the axis 24 through the deployment angle β. Typically, for a deployed configuration of the web member 33, the deployment angle β will be in a range between 60° and 90° (i.e. 60°<β<90°).

An important feature of the present invention is that, in combination, each loop 48 is affixed to the injection needle 28 to avoid overlap and interference with another loop 48 during a configuration transition. In the event, the consequence here is that with a deployment of the web member 33, each independent loop 48a-c will extend to become located at an axial distance "d" from the distal end 30 of the injection needle 28. The result here is to establish a barrier that will prevent the insertion of the injection needle 28 into tissue through a distance greater than "d".

While the particular Injection Needle Insertion Barrier as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A catheter system for performing an injection of fluid medicament into a tissue of a patient which comprises:
    a catheter having a proximal end and a distal end, and formed with a lumen extending therebetween;
    an injection needle positioned in the catheter for reciprocating movement through the lumen of the catheter, wherein the injection needle has a proximal end and a distal end and defines an axis;
    a plurality of loops wherein each loop is an elongated wire having a first end and a second end and a midpoint therebetween to define a loop plane, wherein each end of the loop is affixed to the injection needle at respective points in a plane perpendicular to the axis of the needle, and wherein the loop is biased to transition in the loop plane between a folded configuration inside the catheter and a deployed configuration outside the catheter, wherein for its folded configuration each loop has a first portion extending between the first end of the loop and the midpoint and a second portion extending between the second end of the loop and the midpoint with the first portion aligned parallel to the second portion, and wherein for its deployed configuration the first portion and the second portion of each loop are bowed away from each other to form an elliptically-shaped loop, and wherein during a configuration transition of the loop in the loop plane, each loop plane is independently rotated from the axis of the injection needle through a respective deployment angle β, wherein β is in a range between 60° and 90° and is measured distal to the plane perpendicular to the axis of the injection needle, and further wherein each loop is affixed directly to the injection needle and is confined between the injection needle and the catheter to avoid overlap and interference with another loop during the configuration transition; and
    a relationship formed by the catheter and the injection needle for collectively moving the plurality of loops during their respective configuration transition to create a barrier wherein the midpoints of the loops are located at a distance "d" proximal the distal end of the injection needle to prevent an insertion of the injection needle any deeper than the distance "d" into the tissue of the patient.

2. A system as recited in claim 1 wherein the relationship formed by the catheter and the injection needle for collectively moving the plurality of loops during the configuration transition involves a cooperative interaction between the injection needle and the catheter, and wherein the barrier is created when the injection needle is moved in a distal direction relative to the catheter to advance the distal end of the injection needle beyond the distal end of the catheter.

3. A system as recited in claim 1 wherein the relationship formed by the catheter and the injection needle for collectively moving the plurality of loops during the configuration transition involves a cooperative interaction between the injection needle and the catheter, and wherein the barrier is created when the catheter is moved in a proximal direction relative to the injection needle to deploy the distal end of the injection needle beyond the distal end of the catheter.

4. A system as recited in claim 3 wherein the barrier has a diameter "D" in a flared configuration, and wherein "D"/2 is less than "d".

5. A system as recited in claim 1 wherein when the injection needle is withdrawn into the lumen of the catheter, each loop is constrained by the catheter into its folded configuration, and $\beta=0°$.

6. A system as recited in claim 5 wherein when the injection needle has been advanced beyond the distal end of the catheter, each loop is independently biased through the configuration transition from its folded configuration and into its deployed configuration to create the barrier.

7. A system as recited in claim 1 wherein the barrier is radiopaque and is made of a material selected from a group comprising cobalt chromium, platinum, nitinol and stainless steel.

8. A system as recited in claim 1 wherein the injection needle is smaller than 18 gauge, and the distance "d" is less than 15 mm.

9. A catheter system for performing an injection of fluid medicament into a tissue of a patient which comprises:
   a catheter having a proximal end and a distal end with a lumen extending therebetween, wherein the catheter defines an axis;
   an injection needle having a proximal end and a distal end and defines an axis, with the injection needle received into the lumen of the catheter for alternate proximal and distal axial movements therein; and
   a web member mounted on the injection needle, wherein the web member comprises a plurality of loops wherein each loop is an elongated wire having a first end and a second end and a midpoint therebetween to define a loop plane, wherein each end of the loop is affixed to the injection needle at respective points in a plane perpendicular to the axis of the injection needle, and wherein the loop is biased to transition in the loop plane between a folded configuration when the web member is constrained inside the lumen of the catheter, and a deployed configuration when the web member is advanced in a distal direction beyond the distal end of the catheter, wherein for its folded configuration each loop has a first portion extending between the first end of the loop and the midpoint and a second portion extending between the second end of the loop and the midpoint with the first portion aligned parallel to the second portion, and wherein for its deployed configuration the first portion and the second portion of each loop are bowed away from each other to form an elliptically-shaped loop, and further wherein each loop is affixed directly to the injection needle and is confined between the needle and the catheter to avoid overlap and interference with another loop in the web member during a configuration transition of the loop in the loop plane, and further wherein during the configuration transition of the loop in the loop plane, each loop plane is independently rotated from the axis of the injection needle through a respective deployment angle $\beta$, wherein $\beta$ is in a range between 60° and 90° and is measured distal to the plane perpendicular to the axis of the injection needle, to create a barrier wherein the midpoints of the loops are located at a distance "d" proximal the distal end of the injection needle to prevent an insertion of the needle any deeper than the distance "d" into the tissue of the patient.

10. A system as recited in claim 9 wherein with the injection needle withdrawn inside the lumen of the catheter, and with each loop in the web member constrained by the catheter into its folded configuration, $\beta$ will equal 0°, and when the web member has been advanced beyond the distal end of the catheter, each loop is biased through the configuration transition from its folded configuration and into its deployed configuration to create the barrier.

11. A system as recited in claim 9 wherein the injection needle is smaller than 18 gauge.

12. A system as recited in claim 9 wherein the distance "d" is less than 15 mm.

* * * * *